US005698194A

United States Patent [19]

Hadden

[11] Patent Number: 5,698,194
[45] Date of Patent: Dec. 16, 1997

[54] METHOD FOR MAKING A MEDICAMENT FOR TREATING SECONDARY IMMUNODEFICIENCY

[75] Inventor: John Winthrop Hadden, Tampa, Fla.

[73] Assignee: University of South Florida, Tampa, Fla.

[21] Appl. No.: 610,075

[22] Filed: Feb. 29, 1996

Related U.S. Application Data

[63] Continuation of Ser. No. 341,645, Nov. 17, 1994, abandoned.

[51] Int. Cl.$^6$ .................................................. A61K 45/05
[52] U.S. Cl. .......................... 424/85.1; 424/85.2; 424/85.4; 424/85.5; 435/70.4; 435/70.5
[58] Field of Search .......................... 424/85.1, 85.2, 424/85.4, 85.5; 435/70.1, 70.3, 70.4, 70.5

[56] References Cited

U.S. PATENT DOCUMENTS

| | | | |
|---|---|---|---|
| 4,390,623 | 6/1983 | Fabricius et al. | 435/325 |
| 4,448,879 | 5/1984 | Fabricius et al. | 435/325 |
| 4,464,355 | 8/1984 | Fabricius et al. | 424/101 |

OTHER PUBLICATIONS

Alvarez et al., "Human T cell growth factor" *The Journal of Immunology*, vol. 123, No. 3, pp. 977–984 (1979).
Lafferty et al., "Immunological induction of T lymphocytes: role of antigen and the lymphocyte costimualtor" *Blood Cells*, 4:395–404 (1978).
Talmage et al., "Activation of cytotoxic T cells by nonstimulating tumor cells and spleen cell factor(s)" *Proc. Natl. Acad. Sci. USA*, vol. 74, No. 10, pp. 4610–4614 (1977).
Vine et al. *J. Immunology*, 141(8). 1988, 2593–2600.
Mitchell et al, *J. Immunology* 142(5), 1989, 1548–1557.
Gollapudi et al. *Antimicrob Agents Chemother.* 29(2). 1986 pp. 337–338.
AIS Technical Bulletin No. 9003, "Covalent Immobilization of Antibodies to Protein–Reactive Polystyrene".
Belldegrun and Rosenberg, "Adoptive immunotherapy of urologic tumors" *Cancer Treat. Res.* 46:213–233, 1989.
Bender et al., "Absolute Peripheral Blood Lymphocyte Count and Subsequent Mortality of Elderly Men" *JAGS* 34:649–654, 1986.
BioWhittaker Brochure, "Adoptive Immunotherapy and Genetic Therapy".
Borden, "Interferons: Rationale for Clinical Trials in Neoplastic Disease", *Ann, Int. Med.* 91:492–499, 1979.
Chang and Rosenberg, "Overview of Interleukin–2 as Immunotherapeutic Agent" *Semin. Surg. Oncol.*, 5(6):385–90, 1989.
Chilson and Kelly–Chilson, "Mitogenic Lectins Binds to the Antigen Receptor on Human Lymphocytes" *Eur. J. Immunol.*, 19:389–396, 1989.
Chirigos and Talmadge, "Immunotherapeutic Agents Their Role in Cellular Immunity and Their Therapeutic Potential" *Springer Seminars in Immunopathol.*, 8:327–336, 1985.
Cortesina et al., "Monoclonal Antibodies against Epithelial Antigens . . . " *J. Laryngol Otol.* 102(8):709–12, 1988.

Cortesina et al., "Temporary Regression of Recurrent Squamous Cell Carcinoma of the Head and Neck . . . " *Br. J. Cancer*, 69:572–576, 1994.
Deans et al., "CD45R as a Primary Signal Transducer Stimulating IL–2 and IL–2R mRNA Systhesis by CD3 4 8 Thymocytes" *J. Immunol.*, 143:2425–2430, 1989.
DeSimone et al., "Report of the Symposium on the Use of Intravenous Gammaglobulin (IVIG) in Adults Infected with HIV" *J. Clin. Lab. Anal.* 4:313–317, 1990.
Devos, "Molecular cloning of human interleukin 2 cDNA and its expression in *E. coli*" *Nucleic Acids Res.*, 11:4307–4323, 1983.
Forni et al., "Interleukin 2 Activated Tumor Inhibition in vivo depends on the systemic involvement of host immunoreactivity" *J. Immunol.* 138:4033–41, 1987.
Gillis et al., "T Cell Growth Factor: Parameters of Production and a Quantitive Microassay for Activity" *J. Immunol.*, 120:2027–2032, 1978.
Goldstein and Laslo, "The Role of Interferon in Cancer Therapy: A Current Perspective" *Ca–A Cancer Journal For Clinicians*, 38:258–290, 1988.
Hadden, "Immunotherapy of Human Immunodeficiency Virus (HIV)" *TIPS*, 12:107–111, 1991.
Hadden, "Thymic Endocrinology" *Int. J. Immunopharmacol.*, 14:345–352, 1991.
Hadden, "Immunostimulants" *Immunology Today 276*, vol. 14, No.6, 1993.
Hadden, "T–Cell Adjuvants", *Int. J. Immunopharmacol.*, vol. 16, No. 9, pp. 703–710, 1994.
Hadden and Smith, "Immunopharmacology" *JAMA*, 268:2964–2969, 1992.
Hadden et al., "Lymphocyte Blast Transformation I. Demonstration of Adrenergic Receptors in Human Peripheral Lymphocytes" *J. Cell. Immununol.* 1:583–595, 1970.
Hadden et al., "Strategies of Immune Reconstitution: Effects of of Lymphokines . . . " *Life Sci.* 44:V–XII, 1989.
Hadden et al., "The Characterization of Immunotheraputic Agents" In *Immunopharmology Reviews*, Plenum Press, NY, pp.1–64, 1990.
Hadden et al., "Mixed Interleukins and Thymosin Fraction V Synergistically Induce T Lymphocyte Development in Hydrocortisone . . . " *Cell. Immunol.* 144:228–236, 1992.
Hadden et al., "Interleukins and Contrasuppression Induce Immune Regression of Head and Neck Cancer" *Int. Arch. Otolaryngol.*, 120:395–403, 1994.
Hall, "Immunomodulation with Intravenous Immunoglobulin" *Pharmacotherapy*, 13(6):564–73, Nov.–Dec. 1993.

(List continued on next page.)

*Primary Examiner*—Leon B. Lankford, Jr.
*Attorney, Agent, or Firm*—Kohn & Associates

[57] ABSTRACT

A method of producing a natural nonrecombinant cytokine mixture is disclosed including the steps of immobilizing at least one mitogen in a tissue culture vessel. An isolated population of lymphocytes free of neutrophils and erythrocytes, is suspended in a serum-free media and placed in the vessel. The lymphocytes are cultured, the media removed, and characterized for the yield of cytokines.

9 Claims, 6 Drawing Sheets

OTHER PUBLICATIONS

Hwu and Rosenberg, "The Use of Gene-Modified Tumor-Infiltrating Lymphocytes for Cancer Therapy" *Ann. N.Y. Acad. Sci.* 716:188–203, 1994a.

Hwu and Rosenberg, "The Genetic Modification of T Cells for Cancer Therapy: An Overview of Laboratory and Clinical Trials" *Cancer Detect. Prev.* 18(1):43–50 1994b.

*IGIV News Update*, "An Extra Measure of Viral Safety" vol. 1, No. 2, Dec., 1993.

June et al., "Evidence for the Involvement of Three Distinct Signals in the Induction of IL–2 . . . " *J. Immunol.*, 143:153–161, 1989.

Kameda et al., "Mixed Lymphokines in Low Dose Prolong Life in Cyclophosphamide-Treated Melanoma-Bearing Mice" *Int. J. Innunother.* 8:1–5, 1992.

Lane and Fauci, "Therapeutic Approaches to the Underlying Immune Deficit in AIDS" *Abstracts Int. Conf. on AIDS*, Paris, 1986.

Mattijssen et al. "Clinicial and Immunopathological Results of a Phase II Study of Perilymphatically . . . " *J. Immunother.* 10:63–68, 1991.

Merigan, In: *Combination Anti HIV Therapy in Combination Therapy 2* eds. Garaci and Goldstein, Plenum Press, pp.225–229, 1993.

Mishell and Shiigi, "Selected Methods in Cellular Immunology" *Freeman*, pp. 23–24, 1981.

Morgan et al., "Selective in vitro Growth of T Lymphocytes from Normal Human Bone Marrows" *Science*, 193:1007–8, 1976.

Mule and Rosenberg, "Mechanistic Aspects of Successful Immunotherapy." *Prog. Clin. Biol.*, 244:79–91, 1987.

Mutch and Hutson, "Levamisole in the Adjuvant Treatment of Colon Cancer", *Clin. Pharmacol.* 10:95–109, 1991.

Paetkeau et al., *J. Immunol.*, 117:1320–4, 1976.

Pulley et al., "Intravenous, Intralesional and Endolymphatic Administration of Lympokines in Human Cancer" *Lymphokin Research*, vol.5, Supplement 1, pp. S–157–S163, 1986.

Riesenbeck et al., "Superinduction of Cytokine Gene Transcription by Ciprofloxacin" *J. Immunol.*, 153:343–352, 1994.

Rosenberg et al., "Observations on the systemic administration of autologous lymphokine–activated killer cells . . . " *New Eng. J. Med.* 313:1485–1492, 1985.

Rosenberg, "The development of new immunotherapies for treatment of of cancer using interleukin–2" *Ann Surg.* 208(2):121–135, Aug. 1988.

Rosenberg, in *The Transformed Cell*, p. 109, Putnam Sons, New York, 1992.

Rosenberg, *J. Biol. Resp. Mod.* 3:501–511, 1994.

Spreafico, "Use of levamisole in cancer patients" *Drugs* 19:105–116, 1980.

Symoens and Rosenthal, "Levamisole in the modulation of immune response: the current experimental and clinical state" *J. Reticuloendothel. Soc.* 21:175–219, 1977.

Talmadge et al., in *Screening for Biological Response Modifiers: Methods and Rationale*, Martinus Nijhoff, Boston, pp.121–129 and pp. 181–182, 1985.

Talmadge and Hadden, "An update on immunopharmacology of recombinant and synthetic . . . " in *Immunoregulators in Therapy and Disease* (Marcel Dekker, NY) 1993.

Taniguchi et al., "Structure and expression of a cloned cDNA for human interleukin–2" *Nature*, 302:305–310, 1983.

Thurman et al., *J. Biol. Response Modif.* 5:85–107, 1986.

Webb et al., "Mitogen–induced human lymphocyte activation in serum–free medium" *Clinical Immunology and Immunopathology*, 1:304–310, 1973.

Kovacs et al., "Increases in CD4 T lymphocytes with intermittent courses of interleukin–2 . . . " *New Eng. J. Med.* 332:567–575, 1995.

METHOD FOR MAKING A MEDICAMENT FOR TREATING SECONDARY IMMUNODEFICIENCY

This is a continuation of application Ser. No. 08/341,645 filed on Nov. 17, 1994 now abandoned.

TECHNICAL FIELD

The present invention relates to an improved method of producing a natural mixture of cytokines.

BACKGROUND OF THE INVENTION

In recent years it has become possible to modulate the immune system to improve its response and where components of the system are non-functioning to either partially or completely restore the function of the component. For example, bone marrow transplantation used to replace stem cells or provide missing stem cells can cure severe combined immunodeficiency. In another example, immune cells are removed from cancer patients, treated, and returned to the patient wherein there is tumor regression. (Hwu and Rosenberg, 1994a; Hwu and Rosenberg, 1994b) Further, components of the humeral immune system such as $\gamma$-globulin and intravenous immunoglobulin (IVIG) are finding wide therapeutic applications (DeSimone et al., 1990; Hall, 1993). Other immune system components are also being used as therapeutics. (Hadden and Smith, 1992; Hadden, 1993; Talmadge and Hadden, 1994)

Immunomodulators are compounds that modify immune function or have a positive or negative effect on the activity of the immune system. The use of immunomodulators in clinical medicine includes the reconstitution of immune function (or the correction of immunodeficiency) and the suppression of normal or excessive immune function. A major class of immunomodulators is cytokines. Through recombinant technology, many of the cytokines are now available for clinical use. However, the immune system is complex and the interaction of various components is often necessary to effectively modify immune functions. It would be useful to design preparations that provide the various components and interactions to effectively regulate immune function.

Cytokines are peptide/protein immunomodulators that are produced by activated immune cells including thymus-derived T lymphocytes (T-cells), B lymphocytes and monocyte/macrophages. The cytokines include interleukins (IL-1 through IL-15), colony stimulating factors (CSFs) for granulocytes and/or macrophages (CSF-G, CSF-M, CS-FGM), tumor necrosis factors (TNFs $\alpha$ & $\beta$), and interferons (IFN $\alpha$, $\beta$ & $\gamma$).

Interleukin-2 (IL-2) is a lymphokine initially described as a T-cell growth factor (Morgan et al. 1976). Chemically, IL-2 is a 133 amino acid, 15,000-dalton molecular weight glycoprotein. It is produced by normal peripheral blood lymphocytes, by tonsillar and splenic T lymphocytes, and by large granular lymphocytes. IL-2 induces and supports proliferation of antigen or mitogen stimulated T-cells. In addition to the T lymphocyte stimulating function, IL-2 is important in such processes as the initiation, expansion and regulation of the immune response, the production of gamma-interferon (IFN$\gamma$), the induction of lymphokine-activated killer (LAK) cells, the propagation of cytolytic T-cells, and the augmentation of the killer activity of natural killer (NK) cells.

Recombinant IL-2 (rIL-2) is a non-glycosylated protein that is produced by the human cDNA sequence. The genetically engineered IL-2 may be obtained as described by Taniguchi et al. (1983) and Devos (1983) and U.S. Pat. Nos. 4,604,327 and 4,569,790. A rIL-2 mutein, in which the cysteine at position 125 of the wild-type or native molecule has been substituted with a neutral amino acid, e.g., alanine or serine, may be obtained as described in U.S. Pat. No. 4,518,584 to Mark, et al.

A method for producing and isolating rIL-2 to clinical purity can be found in U.S. Pat. No. 4,569,790 to Koths et al., as well as isolation of native IL-2 from cultured T-cells. Methods for producing natural I1-2 can also be found in U.S. Pat. Nos. 4,390,623; 4,464,355; and 4,448,879. Thurman et al. (1986) disclose that different preparations of partially purified natural IL-2 (nIL-2) and rIL-2 preparations vary significantly in their activity in various biological assays.

Various individual cytokines, both natural and recombinant, have been investigated for the treatment of cancer and other diseases. For example, recombinant interferon $\alpha_2$ (rIFN $\alpha_2$) is approved by the U.S. Food & Drug Administration (FDA) for treatment of Hairy cell leukemia, Kaposi's sarcoma, condyloma accumenata, and chronic hepatitis. Natural IFN$\alpha$s, as a mixture (Alferon®) of the twenty or more made by leukocytes, is licensed for condyloma accumenata. Recombinant IFN-$\gamma$ (rIFN-$\gamma$) is licensed for chronic granulomatous disease. rIL-2 is licensed for renal cell cancer. These and other rIL's and rIFNs are under active evaluation in a variety of diseases including several forms of cancer.

Further, rIL-2 cancer therapy has been explored in many clinics and research centers. Rosenberg and colleagues (Rosenberg et al., 1985; Mule and Rosenberg, 1987; Rosenberg, 1988; Belldegrun and Rosenberg, 1989; Chang and Rosenberg, 1989; Rosenberg, 1994) have reported the use of systemically administered rIL-2 in the immunotherapy of patients with renal cell cancer, and malignant melanoma. Cortesina et al., (1988, 1994) described the effects of loco-regional injections of natural and rIL-2 in head and neck cancer patients and found natural IL-2 to be more effective in yielding tumor regression. Patients given large doses of rIL-2 have suffered life threatening toxicity (Rosenberg et al., 1994).

The development and commercial availability of genetically (recombinant) engineered immunomodulators has accelerated the evaluation of these agents in the cancer clinic. The limited efficacy and significant toxicity associated with high doses of rIL-2, rIFN-$\gamma$, rTNF-$\alpha$, and other monotherapies, suggests reconsideration of natural combinations of cytokines in therapeutic strategies. Furthermore, more than one-hundred different cytokine activities have been identified, which raises significant doubt as to whether immunotherapy, based upon combining recombinant cytokines, has a reasonable probability of success in the cancer clinic in the near future.

For example, while IL-2 can stimulate T lymphocyte proliferation as a T-cell growth factor, a number of other factors including other interleukins and thymic peptides are produced in the thymus and are also considered necessary for T lymphocyte development and function. (Hadden, 1992).

An uncharacterized preparation referred to as a natural interleukin preparation (NI) has been shown by applicant to be effective in promoting T lymphocyte development. This uncharacterized mixed preparation (also referred to as buffy coat interleukin, BC-IL) stimulated the proliferation of prothymocytes, immature and mature thymocytes in vitro more effectively than an equivalent concentration of rIL-2

(Hadden et al., 1989). This NI preparation augmented T lymphocyte development in neonatal mice while rIL-2 was inactive (Hadden et al., 1989). Further, this NI preparation augmented T lymphocyte development and function in hydrocortisone-treated, aged mice while rIL-2 in equivalent dose was inactive (Hadden et al. 1992). Further, an uncharacterized NI mixture in low dose prolonged the life in mice bearing malignant melanoma; rIL-2 in equivalent dose was inactive (Kameda et al., 1992). These findings indicate that natural interleukin mixtures have activity not provided by IL-2.

Attempts to correct T lymphocyte defects have been tried experimentally in a variety of settings including T lymphocyte depletion (lymphocytopenia) and T lymphocyte dysfunction (anergy) occurring in aging, cancer, AIDS, and other immunodeficiencies. For example, rIL-2 and thymic peptides have been used in AIDS (HIV) virus infection with variable results (Hadden, 1991). High dose rIL-2 by continuous infusion has been shown to transiently increase T lymphocyte counts in blood of patients with HIV infection but with considerable toxicity (Lane and Fauci, 1985). Pegylated rIL-2 at one and three million units yielded less toxicity but only minor effects on lymphocyte counts in humans with HIV infection (Merigan, 1993). An NI preparation significantly augmented T lymphocyte counts in lymphocytopenia cancer patients without toxicity (Hadden et al., 1994). These findings indicate that natural interleukins act in humans in low doses to increase T cells without toxicity and that rIL-2, while active at high doses, is too toxic for medical use. These findings also support the extrapolation of murine data to man.

The above suggests that the use of preparations of naturally occurring cytokines may be more efficient in affecting the immune system with less toxicity. However, the preparations that are currently available are not well characterized and are cumbersome to produce as described hereinbelow. In order to reproducible modulate the immune system it would be useful to have well characterized preparations of cytokines free of serum and mitogen that can be produced easily and inexpensively and from which it will be possible to establish a reproducible low-toxicity preparation for clinical use.

U.S. Pat. No. 4,985,241 to Zimmerman et al. discloses the use of a recombinant lymphokine or cytotoxin in combination with a biological modifier such as a free radical scavenger or a metabolic inhibitor in therapeutic and prophylactic treatment of biological damage caused to mammalian hosts by free-radical generation but does not suggest producing a defined mixture of naturally occurring cytokines.

It would therefore be useful to produce a natural or nonrecombinant mixture of cytokines (NCM) from lymphocytes that can be used therapeutically in the treatment of diseases and other conditions which include a reduced function, development and number of T lymphocytes, i.e. cellular immune deficiency. To be therapeutically useful, the NCM must be sterile, endotoxin-free, serum-free, mitogen-free, virus-free and DNA-free to avoid reactions from the recipients. Molecular sieving techniques can remove many of these contaminants. However, the more procedures necessary for production, the higher the cost. Additionally, the more handling steps required, the lower the yield as well as increasing chances of contamination. Therefore, if the NCM can be produced in such a way as to minimize or eliminate any of these contaminants, the more cost-effective the production will be.

The preparation of NI employed in the studies described hereinabove was serum-free and mitogen-free but had to be concentrated 10× prior to use.

Natural Interleukin-2 made as taught in U.S. Pat. Nos. 4,390,623 and 4,464,355 is generated in serum-free media thereby not requiring steps to remove serum proteins. The preparation is described as a serum-free, mitogen-free, natural interleukin-2 having activity relevant to cancer. This material was prepared by exposing the cells only briefly to the mitogen (a pulse technique) originally described by Hadden et al., (1970).

The pulse technique is used to stimulate lymphocytes in tissue culture and to avoid having the mitogen present in the media when it is harvested. The cells are initially cultured for two hours in the presence of a mitogen in a serum-free media. After this incubation the cells are re-isolated and washed three times in media not containing the mitogen and then resuspended at low density in fresh tissue culture serum-free medium without mitogen. The preparation was uncharacterized as to components other than IL-2.

U.S. Pat. No. 4,448,879 to Fabricius et al. also teaches a cell culture process to produce a natural serum-free and mitogen-free IL-2 . The method used buffy coat cells in a roller culture system, or in a system that mechanically recirculates the media. However, the method still requires a step in which the cells are washed free of the mitogen and serum and then recultured in a serum-free, mitogen-free media. Importantly, the methods described are only poorly effective to stimulate the cells and produce low yields of IL-2 . The large volumes necessary are expensive and require extensive skilled handling and must be concentrated prior to use resulting in loss of activity (approximately 50%).

Martorell, et al (1987) provides a method of inducing mitogenesis with the continuous presence of mitogen in media containing serum. In their method the yield of IL-2 is extremely low and requires the presence of serum.

It would be useful to have a method which does not require the step of washing the cells free of serum and mitogen and does not require expensive equipment.

In the systems described hereinabove, the mitogens are generally plant lectins such as phytohemagglutinin (PHA) and concanavalin A (Con A) which have an affinity for the T lymphocyte antigen receptor (TCR) (Chilson and Kelly-Chilson, 1989) and have a mitogenic effect upon the T lymphocyte. Exposure of T lymphocytes to such lectins stimulates the production of natural cytokines. In the absence of serum in the culture media, generally only low levels of cytokines, particularly the interleukins, are produced. For example, IL-2 is generally found only in the range of 0–20 units/ml units per milliliter under serum-free culture conditions (U.S. Pat. Nos. 4,390,623 and 4,464,355). With serum, the range of IL-2 production is generally 10 or more units per ml.

It would be useful to stimulate lymphocytes to produce cytokines such as IL-2 at higher levels in the absence of serum so that the mixture can be more efficiently used as a therapeutic agent and without the added step and decreased yield of washing the cells after a pulsed exposure to the mitogen or using specialized equipment to concentrate the preparation with the associated loss of activity.

SUMMARY OF THE INVENTION AND ADVANTAGES

The present invention provides a unique method of producing a natural nonrecombinant cytokine mixture by the steps of immobilizing at least one mitogen in a tissue culture vessel. An isolated population of lymphocytes free of neutrophils and erythrocytes is suspended in a serum-free media and placed in the vessel. The lymphocytes are cultured, the mitogen-free and serum-free media removed and characterized for the yield of cytokines.

BRIEF DESCRIPTION OF THE FIGURES

Other advantages of the present invention will be readily appreciated as the same becomes better understood by reference to the following detailed description when considered in connection with the accompanying figures wherein.

DETAILED DESCRIPTION OF THE PREFERRED EMBODIMENT

Figure 1:
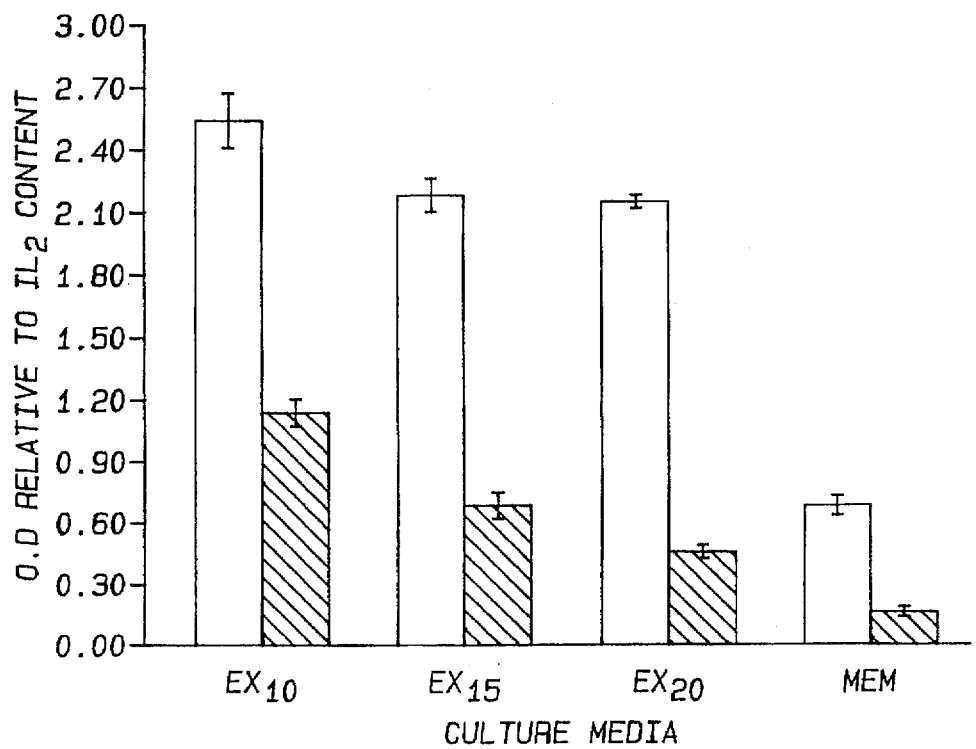
FIG. 1 is a bar graph showing the ILs content (expressed as optical density of IL-2 ($IL_2$) measured by ELISA) of NCM in X-vivo-10 ($EX_{10}$), X-vivo-15 ($EX_{15}$), X-vivo-20 ($EX_{20}$) and minimal essential media (MEM) and comparing continuous exposure (open bar) with pulsed exposure (cross-hatched) to the mitogen PHA.

The present invention provides a method of reproducibly producing a characterized natural nonrecombinant cytokine mixture (NCM), i.e. a cell culture supernatant containing multiple cytokines.

Pooled lymphocytes, generally from the buffy coat, free of neutrophils and erythrocytes from HIV-negative, hepatitis virus-negative multiple donors are used to produce the cytokine mixture of the present invention. The use of multiple donors takes advantage of the mixed lymphocyte response (MLR). Further, in a preferred embodiment up to fifty donors would be used each time to produce the mixture to ensure that the MLR response is constant for each preparation and to even out variation.

In an alternative embodiment, autologous lymphocytes would be used to generate the NCM. In these cases the patient would not have to be virus free. Further, if autologous lymphocytes are used they could be returned to the patient as needed. In an alternative embodiment, animals could be the cell source for veterinary uses.

The lymphocytes are cultured in the presence of immobilized mitogens in a tissue culture vessel. In a preferred embodiment, the mitogen is immobilized on surface activated cell culture flasks for selection of cell subsets (AIS MICROCELLECTOR™ T-25 plates) as described in the manufacturer's instructions. However, other methods of immobilizing mitogens on the surface of the culture vessel such as methods incorporating other "panning" techniques or coupling to sepharose 4B beads could be used as are well known in the art of cell isolation. The use of immobilizing cells for selection is well known in the art; however, the use for cytokine generation is novel.

The mitogens are generally selected from lectins and monoclonal antibodies that stimulate lymphocytes to produce cytokines. In a preferred embodiment, phytohemagglutinin (PHA) or OKT3 (Orthoclone®, Ortho Pharmaceuticals) are used. Other lectins such as concanavalin A (Con A) or pokeweed mitogen which stimulates B cells can be used. Monoclonal antibodies to T-cell receptors such as CD2, CD28, CD45 can be used as mitogens and would be effective. Anti CD28 and CD45 antibodies are reported to be hyperproducers of IL-2 (Deans et al., 1989 and June et al., 1989). Further, antilymphocyte globulin (ALG) has mitogenic activity for T-cells. In addition, combinations of mitogens could be used to activate a combination of lymphocyte subpopulations. PHA is used in the preferred embodiment and is coated at a starting concentration of about 25 µg/ml.

The lymphocytes are incubated for 24–48 hours in a serum free media with continuous exposure to the mitogen, i.e. no washings. In a preferred embodiment the media is either X vivo-10 or X vivo-15 media (Whittaker). This is a serum-free and FDA-approved media for IL-2 /LAK infusions in patients as set forth in the manufacture's brochure. Serum-free media capable of supporting human lymphocyte proliferation like RPMI-1640 (Sigma) could also be used.

The media also contains a 4-aminoquinolone antibiotic. In the preferred embodiment, the antibiotic is ciprofloxacin. The antibiotic is used to maintain sterility and to hyperproduce lymphokines. Ciprofloxacin and related antibiotics have been reported to increase IL-2 and other cytokines in the presence of soluble mitogen and serum. (Riesenbeck et al., 1994) They have not been reported to be effective in the absence of serum. Their use with immobilized mitogens is also novel. Ciprofloxacin is used in the preferred embodiment at a concentration of from about 20 to about 200 µg/ml and more preferably, at a concentration of about 80 µg/ml.

The supernatant is removed and is the source of the natural nonrecombinant cytokine mixture (NCM) of the present invention. The supernatant is free of the mitogen as shown in Example 1 and in animal and initial human studies does not have to be concentrated.

Human serum albumin (HSA) can be added to stabilize the NCM in the supernatant. HSA is used instead of serum albumin from a non-human source because HSA has been approved by the FDA for human use.

A cytokine profile of the supernatant is established utilizing the following assays. The interleukin (IL) content of the supernatants is confirmed by bioassay for IL-2 and by ELISA's for other interleukins, CSFs, TNFs, and IFNs. Sterility is tested and endotoxin measured by limulus lysate assay. Specifically, the following assays and kits are used in a preferred embodiment: INF-γ ELISA (ENDOGEN), IL-1, IL-2, IL-3, IL-4, IL-6, IL-7, IL-8, GM-CSF, G-CSF and TNF-α ELISAs (R&D Systems). The IL-2 bioassay is by the method of Gillis et al. (1978) and is expressed as units/ml compared to a known standard of IL-2 (Schiapparelli Biosystems, Inc., Fairfield, N.J.).

In the preferred embodiment, wherein PHA is used as the mitogen, the cytokine profile for the supernatant has a profile of:

| CYTOKINE | AMOUNT |
| --- | --- |
| IL-1 | 10–2000 pg/ml |
| IL-2 | 100–500 units/ml |
| IL-6 | 250–10,000 pg/ml |
| IL-8 | 12,000–100,000 pg/ml |
| IL-12 | 100–10,000 pg/ml |
| IFN-γ | 50–15,000 pg/ml |
| TNF-α | 50–15,000 pg/ml |
| CSF-G | 50–1500 pg/ml |
| CSF-GM | 10–1500 pg/ml |
| IL-3/IL-4/IL-7 | Trace Amounts |

Immobilization of the mitogen produces a higher yield of NCM than does the pulse techniques of the prior art. For example, production of interleukins by a pulse technique with PHA in serum-free media yielded IL-2 at 0–20 units/ml media (U.S. Pat. Nos. 4,390,623 and 4,464,355).

However, the present invention allows an increased production with a pulse technique by adding a 4-aminoquinolone antibiotic to the serum-free media to hyperinduce interleukin yielding IL-2 of about 8–140 units/ml. As predicted by the animal studies previously cited, this preparation, characterized as a natural interleukin mixture (NIM), at 200 units IL-2 /dose, increased T lymphocyte counts in blood of lymphopoenic patients with head and neck cancer (Hadden et al., 1994) which has not been reported for rIL-2 at such a low dose. Similar effects of IL-2 have been reported only at doses greater than 5000 times the amount of IL-2 in NCM. Thus, it is important to note that the dose of IL-2 equivalent for NCM is used as an index of its potency and is not meant to imply that the total biological activity of NCM is that of only IL-2.

In the preferred embodiment of the present invention, utilizing continuous exposure to the mitogen by immobilization and the presence of a 4-aminoquinolone antibiotic, the NCM which is generated generally contains IL-2 at 100–353 units/ml (an index of the potency of the preparation). In the less preferred embodiment the invention can be practiced with the continuous presence of 4-aminoquinolone antibiotic and a pulsed presence of the mitogen, producing NIM. This combination produces a level of cytokines greater than the prior art with a pulsed mitogen only, but does not produce the levels seen with the preferred embodiment of the present invention (NCM): continuous immobilized mitogen and 4-aminoquinolone antibiotic. The preferred embodiment in this situation is defined by the potency of the cytokine preparation not requiring concentration resulting in loss of biological activity. The preferred embodiment at equivalent doses of IL-2 has the same biological activities as the less preferred embodiment (NIM or NI) (see Hadden et al. (1992) and co-pending application U.S. Ser. No. 341,424 by the same applicant filed the same day as the present applications and assigned to the same assignee of the present invention).

The production of mixtures of natural cytokines by lymphocytes stimulated with PHA is representative of plant lectins having affinity for the T lymphocyte antigen receptor (TCR). Another such stimulant is concanavalin A (Con A). It would similarly be expected to induce high levels of interleukins under these conditions. The production of mixtures of natural cytokines by a monoclonal antibody such as OKT-3 which binds to T lymphocyte surface receptors related to the TCR i.e., the CD3 complex, is representative of other monoclonal antibodies to such receptors as CD2, CD28, CD45 and they would similarly be expected to induce high levels of cytokines under these conditions. Other mitogens which stimulate B cells or monocytes could be used in combination with mitogens which stimulate T-cells to provide a natural nonrecombinant cytokine mixture.

It would be expected that combinations of these stimulants would have additive effects as observed in Table III for IL-1 and IL-2.

The observation contained herein that the NCM produced by PHA is rich in IL-1, IL-2, IFN-γ, and also contains IL-12 (323 pg/ml), and has only trace amounts of IL-3, IL-4, and IL-7 indicates that under these conditions PHA stimulates preferentially T-helper type I cells (TH-1) over T-helper type II cells. This allows the determination that these lymphokine preparations will have adjuvant activity to augment cellular immune responses (see Hadden, 1994). The production of NCM with immobilized mitogens can be utilized with T-cell subsets (CD4, CD8, CD30, TH-1, THE-2, etc.) using the appropriate plates for cell separation by panning prior to stimulation with PHA or other mitogens to obtain NCM that are enriched for cytokines specific to these cell types.

The NCM is aliguoted and stored at 4° C. or less to maintain biological activity.

An effective amount of a natural recombinant cytokine mixture according to the invention protocol and as set forth in the co-pending application U.S. Ser. No. 341,424 by the same applicant, filed the same day as this application and assigned to the same assignee as this application and incorporated herein by reference. The natural nonrecombinant cytokine mixture can be administered to a mammalian host, preferably human, and will have a specific cytokine profile and will generally have about 200–500 Units per dose of IL-2 for humans.

The patients to receive the treatment will be those with diagnosed cellular immune deficiencies either by itself or in combination with other disease states. The patient's T-cell function and blood levels will be evaluated as is known in the art and if below normal will be a candidate for the treatment as having a cellular immune deficiency with the present invention designed to specifically treat the T-cell abnormality. It is important to note the T cell lymphocytopenia is not only a reflection of cellular immune deficiency in disease such as cancer and AIDS, but it is also a predictor of mortality in elderly men without disease (Bender et al., 1986).

The NCM is administered at low doses (200–500 units) of IL-2 equivalence in accordance with good medical practice, taking into account the clinical condition of the individual patient, the site and method of administration, scheduling of administration, and other factors known to medical practitioners. The "effective amount" for purposes herein is thus determined by such considerations as are known in the art. It is important not to use high doses (>1000 units/dose) as effect is lost and toxicity increases. The amount must be effective to show improvement in immune function in 25% of patients treated including, but not limited to, improved responses in in vitro measurements of cellular immune function, increased T lymphocyte levels in vivo, improved skin test response to recall antigens or NCM, improved survival rate, more rapid recovery, or improvement or elimination of symptoms and in cancer reduction of tumor mass. NCM may be used with other treatments to improve immune function and treat cancer. Example of the clinical use of NCM or NIM is exemplified by Hadden et al., (1994) in head and neck cancer.

In the method of the present invention, the NCM can be administered in various ways. It should be noted that NCM can be administered alone or in combination with pharmaceutically acceptable carriers. It can be administered subcutaneously or parenterally including intravenous, intraarterial, intramuscularly, intraperitoneally, perilymphatic, intralymphatic, and intranasal administration. Site specific administration is preferred if possible. Implants or infusion of the compounds are also useful. Guidance is provided by Hadden et al. (1990) and Hadden et al. (1994).

For parental administration in humans, the present invention will generally be formulated in unit dosage injectable form, preferably in a pharmaceutically acceptable carrier medium and in a preferred embodiment it will be X-vivo-10 media. Suitable carrier media can also include, but are not limited to, saline, squalene, dextrose solution, normal serum albumin, Ringer's solution, and the like. Optionally, minor amounts of additives such as, for example, stabilizers, preservatives or buffers may be included in such vehicle. Such formulation is suitable for reconstruction in aqueous injections for parental administration. The mixture will typically be formulated in the carrier medium at a concentration of about 50 to 500 units of IL-2 (equivalency)/ml, preferably from about 150 to 350 units of IL-2 (equivalency) /ml. Further the mixture will have a consistent profile for other cytokines as set forth for the present invention.

Optionally, the NCM may be brought into a sterile, stable lyophilized formulation in which the active ingredients are admixed with a water-soluble carrier, and optionally, stabilizer or non-toxic preservatives. These various additives which enhance the stability, sterility, and isotonicity of the compositions, including antimicrobial preservatives, antioxidants, cheating agents, and buffers, can be added. Prevention of the action of microorganisms can be ensured by the presence of ciprofloxacin and by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive or delivery vehicle used would have to be compatible with the NCM and not alter the biological activity of the present invention.

The dose and dosage regimen will depend mainly on the individual patient being treated, the history of the patient, the type and magnitude of biological damage to the patient, the length of treatment and the protocol of the treatment. The doses may be single dose or multiple doses over a period of several days. The most preferred doses are those which achieve maximum regression of disease in the case of cancer or maximum reduction of symptoms in other disease states. It is noted that humans are treated generally longer than the mice exemplified herein which treatment has a length proportional to the length of the disease process and drug effectiveness.

A pharmacological formulation of the NCM can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as infusion pumps, polymer matrices, liposomes, and microspheres. An implant suitable for use in the present invention can take the form of a pellet, which slowly dissolves after being implanted or a biocompatible delivery module well known to those skilled in the art. Such well known dosage forms and modules are designed such that the active ingredients are slowly released over a period of several days to several weeks.

For example, such slow release forms on infusion delivery systems would be envisioned to be employed in lung and esophageal cancer so as to deliver the NCM herein described to the regional nymph nodes in the vicinity of cancer. Other cancers would use similar regional delivery techniques.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

The present invention is effective to increase thymocyte numbers and function and to reverse secondary immunodeficiency as occurs in cancer, HIV, infection, aging, etc. The method may be used to treat patients on an in-patient as well as out-patient basis, the latter being preferable.

The above discussion provides a factual basis for the making of a natural nonrecombinant cytokine mixture (NCM). The methods used with and the utility of the present invention can be shown by the following examples.

The examples demonstrate the utility of the invention in the murine system; however, equivalent preparations (NI and NIM) have demonstrated activity on the immune system of man (Pulley et al., 1994; Hadden et al., 1994). The mouse system was chosen because, besides man, the mouse is the best studied species for structure and function of the immune system and is accepted by those skilled in the art as highly predicative of human response. So far, only minor differences have been observed between mice and man. Most of the mechanisms by which the mouse defends itself against various pathogens and tumors are essentially the same as for man. Mouse models have been extensively employed in the evaluation of immunodulators for use in humans (Talmadge et al., 1985). Because of this prior art, results from current murine experiments are predictive of human responses.

Three examples demonstrate the predictive nature of the murine system with immunomodulators. Using a broad spectrum of murine tumor models the antitumor activity of interferons (IFNs) has been shown (Borden, 1979; Talmadge et al, 1985) and correspondingly in humans, IFNs have shown activity against a large variety of tumors (Goldstein and Laslo, 1988).

In a second example, using murine tumor models there was no effect of levamisole used alone on tumors but activity was seen following chemotherapy (Symoens and Rosenthal, 1977; Spreafico, 1980). Similarly in humans, levamisole showed activity in human colon cancer when used with 5 fluorouracil, but not alone (Mutch and Hutson, 1991).

In a third example, using murine tumor models low dose interleukin 2 (IL-2 ) was shown to have antitumor activity without toxicity while high dose IL-2 had activity especially with lymphokine activated killer (LAK) cells (Rosenberg et al, 19850, but with potentially lethal toxicity. Human studies also showed the effectiveness of high dose IL-2±LAK cells in malignant melanoma and renal cell cancer but with great toxicity (Rosenberg, 1994). Even so, it is now licensed by the FDA for renal cell cancer. Recent studies show effectiveness of low dose IL-2 in human cancer without toxicity (Cortesina et al., 1988 and 1994). The mechanisms are similar to the low dose effect seen in the murine system (Chirigos and Talmadge, 1985).

The above three examples of immunomodulators are now approved for clinical use in cancer and were well predicted by murine tumor studies.

In addition, animal studies have shown effects of natural interleukin mixtures (nILs) not shared by recombinant interleukins (rILs). nILs, but not rIL-2, are active to restore and promote thymus dependent immune responses (Hadden et al, 1992) and to promote resistance to malignant melanoma with cyclophosphamide. (Kameda et al, 1992) This same pattern has been seen in humans in that natural ILs were active in human head and neck cancer in a way not shared by recombinant IL-2. (Cortesina, 1988, 1994; Hadden et al, 1994; Mattijissen et al., 1991).

EXAMPLES

General Methods:

All steps relating to cell culture are performed under sterile conditions. General methods of cellular immunology not described herein are performed as described in general references for Cellular immunology techniques such as Mishell and Shiigi (Selected Methods in Cellular Immunology, 1981) and as are known in the art.

Materials

Recombinant human interleukin beta 1 (rIL-1 beta) was a gift from Dr. C. Reynolds, Biological Response Modifiers Program, NCI (Frederick, Md.). Human interleukin 2 (IL-2; specific activity 640 U/ml) was obtained from Pharmacia AB (Silver Spring, Md.). Recombinant IL-2 was a gift from G. Caspritz (Hoescht Pharm., Frankfort, Germany). Ciprofloxacin was purchased from Miles Inc., (West Haven, Conn.); Ofloxacin from McNeil Pharmaceutical (Spring House, Pa.); and Norfloxacin from Merck & Co. (West Point, Pa.). Human serum albumin (HSA) was obtained from Armour Pharmaceuticals (Kankakee, Ill.). X-vivo media was purchased from Whittaker Bioproducts (Walkersville, Md.). Hydrocortisone 21-hemisuccinate and Con A were purchased from Sigma Chemicals (St. Louis, Mo.). PHA (HA-16) was obtained from Murex Diagnostics Ltd., (Dartford, U.K.). OKT3 was purchased from Ortho Pharmaceuticals (Raritan, N.J.).

Preparation of natural cytokine mixture (NCM)

The buffy coat white cells of human blood from multiple HIV-negative hepatitis virus-negative donors is collected. In an alternative embodiment, animals could be the cell source for veterinary uses. The cells from the donors are pooled and layered on ficoll hypaque gradients (Pharmacia) to yield lymphocytes free of neutrophils and erythrocytes. (U.S. Pat. No. 4,390,623 and 4,448,879) Alternative methods could be used that would result in the same starting lymphocyte population as are known in the art.

The lymphocytes are washed and distributed in X vivo-10 media (Whittaker Bioproducts) to surface activated cell culture flasks for selection of cell subsets MICROCELLECTOR™ T-25 Cell Culture Flasks) in which are immobilized stimulants, i.e. mitogens. In one set of experiments, X vivo-15 and X vivo-20 media were used as indicated. The immobilization process for the stimulants is as described by the manufacturer for immobilizing various substances for panning procedures, i.e. separating cells, in the flasks.

The cells are incubated for 24–48 hours in X vivo-10 media with 80 µg/ml ciprofloxacin (Miles Lab) at 37° in a $CO_2$/air incubator. Alternatively, RPMI 1640 media could be used (Webb et al. 1973). Generally the HSA is used at 0.1 to 0.5% (weight by volume). Following incubation the supernatants are poured off and collected. Human serum albumin (HSA) can be added to stabilize further the interleukins. The supernatants are stored at 4° C. to −70° C.

Characterization of Supernatants

The pooled supernatants are characterized by measuring the cytokine content by bioassay for IL-2 and ELISAs for the remaining interleukins IL-1–IL-15, CSFs, TNFs, and IFNs. Sterility is tested by culture in thioglycolate broth and endotoxin measured by limulus lysate assay as is known in the art.

Standardization of supernatant for cytokine content

Each supernatant is standardized either by concentration or amount administered so that comparisons can be made.

Removal of contaminants for supernatant

DNA and virus exclusion, if used, will employ such techniques as ultrafiltration, column chromatography, virasol, ethanol fractionation, polyethylene glycol/bentonite precipitation, gamma irradiation, and/or solvent/detergent treatment as has been used for intravenous gamma globulin and monoclonal antibodies (e.g. IGIV News Update brochure).

Model

The model of hydrocortisone induced thymic involution in aged mice was used unless otherwise indicated (Hadden et al., 1992).

Laboratory Animals

Female BALB/c (Life Science, St. Petersburg, Fla.) aged retired breeder mice (8–9 months) whose thymuses had begun to involute were employed in in vivo tests. Mice were weight matched and randomly pooled in groups of five. Animals were fed standard laboratory diets with drinking water ad lib. All mice, with exception of a control group, were treated intraperitoneally (i.p.) with hydrocortisone (5 mg/mouse in 0.1 ml 0.9% sodium chloride) for two consecutive days to induce a chemical thymectomy and reduction of spleen weight.

Hydrocortisone-treated adult mice show acute thymic involution (less than 30% of control) and reduction in spleen size (less than 80% of control) at two days with progressive recovery to 10 days.

Experimental Design

Each treatment group had five (5) animals and each experiment was repeated 2–5 times. Treatment was initiated intraperitoneally (i.p.) on Day 3 and continued once per day for a total of five (5) days. Treatment groups were injected with one of the following in vivo treatments as indicated in the text:

1. pyrogen free saline (controls);
2. recombinant interleukin-1 (rIL-1; 4 ng);
3. recombinant interleukin-2 (rIL-2; 50 units);
4. rIL-1+rIL-2 (4 ng+50 units, respectively)
5. natural cytokine mixture (NCM; 50 units IL-2 equivalence)

On day 8, the mice were weighed, sacrificed by cervical dislocation, and their spleens and thymuses removed and weighed. The organs were minced, the residual erythrocytes were lysed using ammonium chloride (Mishell and Shiigi 1981), and the cells counted.

The proliferative response of the cells to various substances was then determined. A sample of cells was prepared for cell culture at 37° C., 5% $CO_2$ in RPMI 1640 medium with 5% fetal bovine serum, penicillin (100 U/ml), streptomycin (100 μg/ml) and 2-mercaptoethanol ($2\times10^{-5}$ M). The cells were plated in 0.2 ml microwell plates in quadruplicate at a concentration of $1.5\times10^6$/ml and incubated for 72 hours with one of the following as indicated in the text:

1. control diluent (complete RPMI 1640 medium);
2. rIL-1 (1 ng/ml);
3. rIL-2 (2 Units/ml);
4. NCM (2 Units/ml of IL-2 equivalence)
5. concanavalin A (Con A; 1.5 μg/ml)
6. phytohemagglutinin (PHA; 0.5μg/ml)

The culture was terminated to measure DNA synthesis, thus cell prolifation, with an 18 hours pulse of tritiated thymidine (3H-Thymidine; New England Nuclear, Boston, Mass.; specific activity 6.7 Ci/mM), harvested with a multiple automatic sample harvester and processed for liquid scintillation counting. Marker studies were also performed as described by, Hadden et al. (1992). The results were expressed as arithmetic mean of cpm from three samples for each animal. In order to simplify the representation of data obtained with different animals, the results with the different animals were pooled and calculated together and in some cases are expressed as ratio to control and others as means+ brackets for standard error of the mean (SEM).

Statistical Analysis

Student's T test was used to analyze data as appropriate.

Example 1

The objective was to find a way to stimulate lymphocytes to produce high levels of interleukin-2 in the absence of serum and in a way which did not yield significant quantities of PHA in the supernatant. To do this, the PHA was immobilized on surface activated cell culture flasks for selection of cell subsets (AIS MICROCELLECTOR™ T-25 plates) as described in the manufacturer's instructions for "panning" cell separation.

Media employed in these experiments was X vivo-10 (Whittaker) and is approved for administration to humans by the U.S. Food and Drug Administration for interleukin-2 -lymphokine activated killer (LAK) cell protocols. Serum-free media capable of supporting human lymphocyte proliferation like minimal essential media (MEM) or RPMI-1640 (Sigma) could also be used.

Initial experiments indicated that PHA (HA-16, Murex Diagnostics Ltd., Dartford, U.K.) could be immobilized by the technique described by the manufacturer and that under appropriate optimal conditions of cell number of $7.5-15\times10^6$/ml, time of exposure of 24 hours–48 hours, and PHA concentration of 25 or 50 μg/ml a high yield of interleukin-2 in the serum-free supernatant could be obtained. The yield was superior to previous methods (pulse technique) employing brief exposures to PHA (NI) followed by washing and subsequent culture with ciprofloxacin (NIM) in serum-free media (Table 1). Therefore this flask procedure is used to generate the NCM mixture.

TABLE I

|  | IL content of supernatant/ml |
| --- | --- |
| PHA brief exposure(NI) | 2–20 units |
| PHA brief exposure & ciprofloxacin (NIM) (80 μg/ml) | 8–140 units |
| PHA flask immobilization & ciprofloxacin (80 μg/ml) | 100–353 units |

IL-2 content was measured in the supernatant using the CTLL IL-2 dependent cell line by the methods described by Gillis et al. (1978). IL-2 was quantitated in international units against a known standard containing 640 units (Pharmacia AB).

The cell free supernatants from flasks incubated without cells were tested on human lymphocytes to determine if residual PHA was present in sufficient quantities to produce a proliferative response. Any residual PHA greater than 0.01 μg/ml would give such a response. In the absence of cells, small amounts of PHA were observed in the supernatant at 40–48 hours; however, when PHA (25 μg/ml) was used for only 24 hours, these levels were negligible. 24 hours incubation was thus considered optimal.

When new flasks were compared to outdated flasks under comparable conditions, a higher level of IL-2 was observed with the older flasks. Therefore, outdated flasks were generally but not always used in the examples to generate the NC mixture.

Example 2

Figure 2:
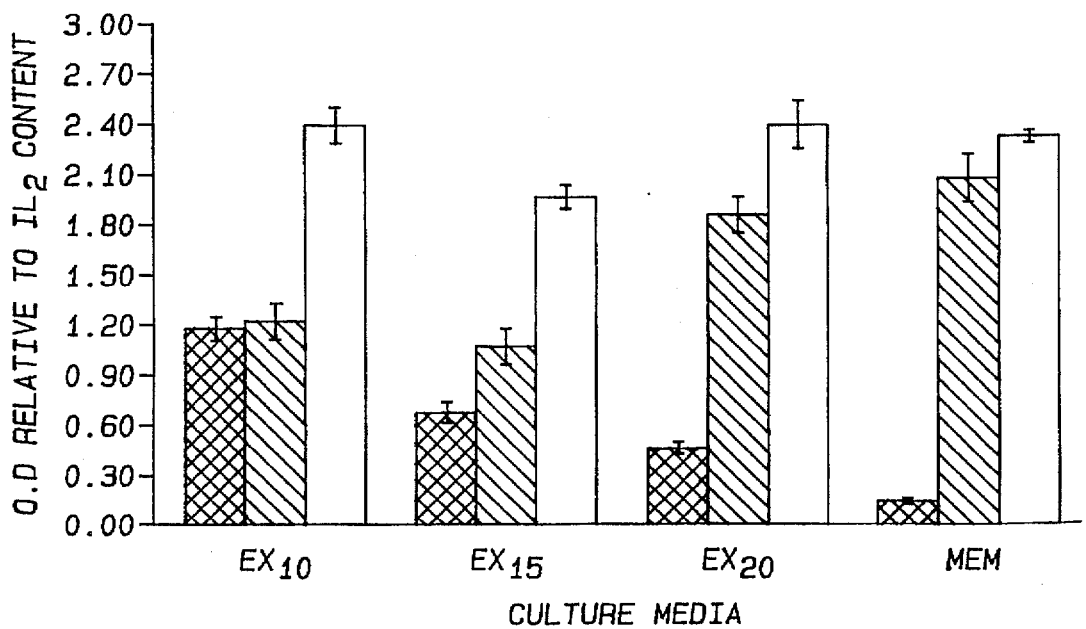
FIG. 2 is a bar graph showing the effect of cell concentration on NCM generation with PHA at 1 µg/ml in different media, $1\times10^6$/ml cells (cross-hatched), $2.5\times10^6$/ml cells (diagonal lines) and $5\times10^6$/ml cells (open bar)
Figure 3:
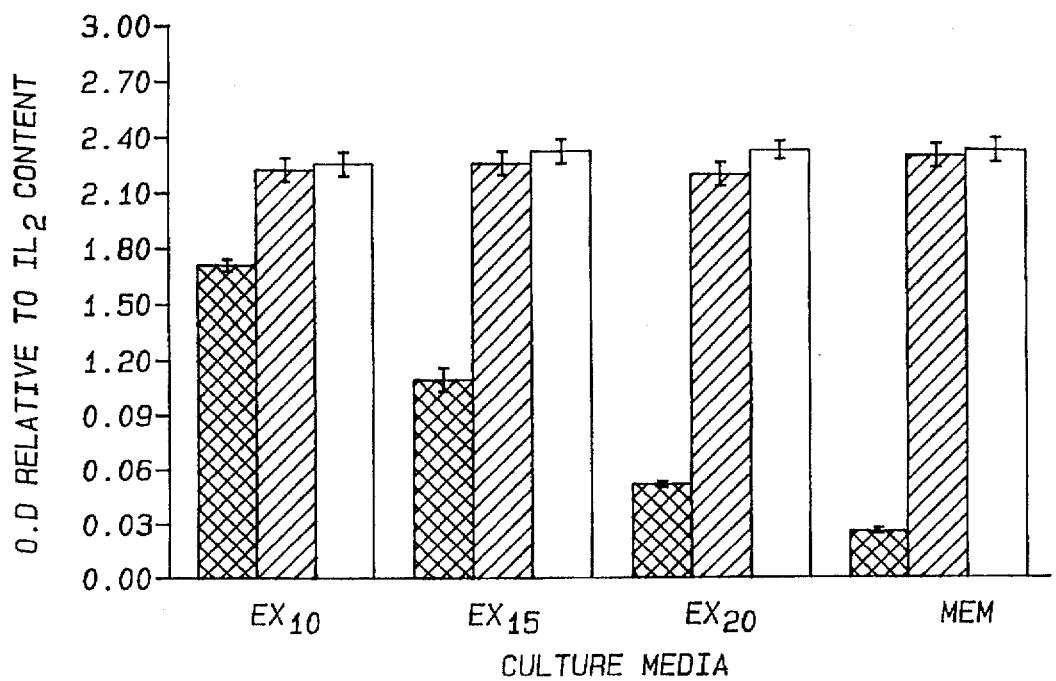
FIG. 3 is a bar graph showing the effect of cell concentration on NCM generation with PHA at 2 µg/ml in different media, $1\times10^6$/ml cells (cross-hatched), $2.5\times10^6$/ml cells (diagonal lines) and $5\times10^6$/ml cells (open bar)

A comparison of X vivo-10, X vivo-15 and X vivo-20 (Whittaker) and MEM in the present invention was undertaken and shown in FIGS. 1–3. X vivo-10 and X vivo-15; are approved for administration to humans by the U.S. Food and Drug Administration for interleukin-2 -lymphokine activated killer (LAK) cell protocols. Generation of NCM was compared in different media utilizing continuous vs pulsed exposure to PHA at 1 μg/ml (FIG. 1). The effect of cell concentration was explored with continuous exposure to PHA at 1 μg/ml (FIG. 2) and PHA at 2 μg/ml (FIG. 3). The optimal combination of these factors was found to be continuous exposure by immobilization in X-vivo-10 at cell concentrations of 2.5 or $5.0\times10^6$/ml with PHA at 2 μg/ml or at $5\times10^6$ cells/ml with PHA at 1 μg/ml. Because the per cell yield is most efficient at $2.5\times10^6$ cell/ml, that concentration with PHA at 2 μg/ml is chosen as the optimal.

Example 3

Preliminary experiments, in tubes rather than flasks, were performed to determine the parameters for ciprofloxacin and two other 4-aminoquinolone antibiotics (Norfloxacin and Ofloxacin) to enhance cytokine production from human leukocytes following exposure to PHA. Table II shows that 80 μl/ml of each of these 4-aminoquinolone antibiotics enhanced production of IL-1, IL-2, IL-6, IFNδ, TNFα, and G-CSF. IL-8 production was maximal. IL-3, IL-4, and IL-7 were undetectable under these circumstances in all supernatants. These results indicate that under these serum free conditions all 4-aminoquinolones tested at 80 μg/ml enhanced PHA induced cytokine production under serum-free conditions.

TABLE II

|  | PHA Alone | Ciprofloxacin & PHA | Norfloxacin & PHA | Ofloxacin & PHA |
|---|---|---|---|---|
| IL-1-β | 81 | 1080 | 783 | 810 |
| IL-2 | ND | 120 | 32 | 82 |
| IL-6 | 1665 | >3000 | >3000 | >3000 |
| IL-8 | 18000 | >18000 | >18000 | >18000 |
| IFNγ | ND | 750 | 210 | 380 |
| TNF-α | 54 | 1935 | 1500 | 4000 |
| GN-CSF | 114 | 4.5 | 4.5 | 72 |
| G-CSF | 41 | 555 | 800 | 630 |

Units for cytokines other than IL-2 are pg/ml and for IL-2 international unit/ml.
ND: not detectable.

Example 4

It was also determined that a monoclonal antibody, OKT-3, (Ortho) which induces T lymphocytes to proliferate and produce interleukins could be employed as a stimulant under these conditions. Table III shows that OKT-3 induced cytokines similar to those induced by PHA plus ciprofloxacin with cells incubated in flasks as set forth in Example 1. IL-3,4 and 7 were not detected with either set of stimulants. OKT-3 produced a small additive effect for several ILs when joined with PHA and ciprofloxacin (CIPRO).

TABLE III

|  | CIPRO + PHA | OKT-3 + CIPRO + PHA | OKT-3 |
|---|---|---|---|
| IL-1-β | 1080 | 1530 | 1125 |
| IL-2 | 120 | 340 | ND |
| IFN-γ | 750 | 4660 | 11280 |
| IL-6 | >3000 | >3000 | 1980 |
| IL-8 | >18000 | >18000 | >18000 |
| TNFα | 1935 | 2700 | 2500 |
| GM-CSF | 4.5 | 12 | 75 |
| G-CSF | 555 | 375 | ND |

Units of interleukins other than IL-2 are pg/ml and for IL-2 international units/ml.
ND-not detectable.

Example 5

Figure 4:
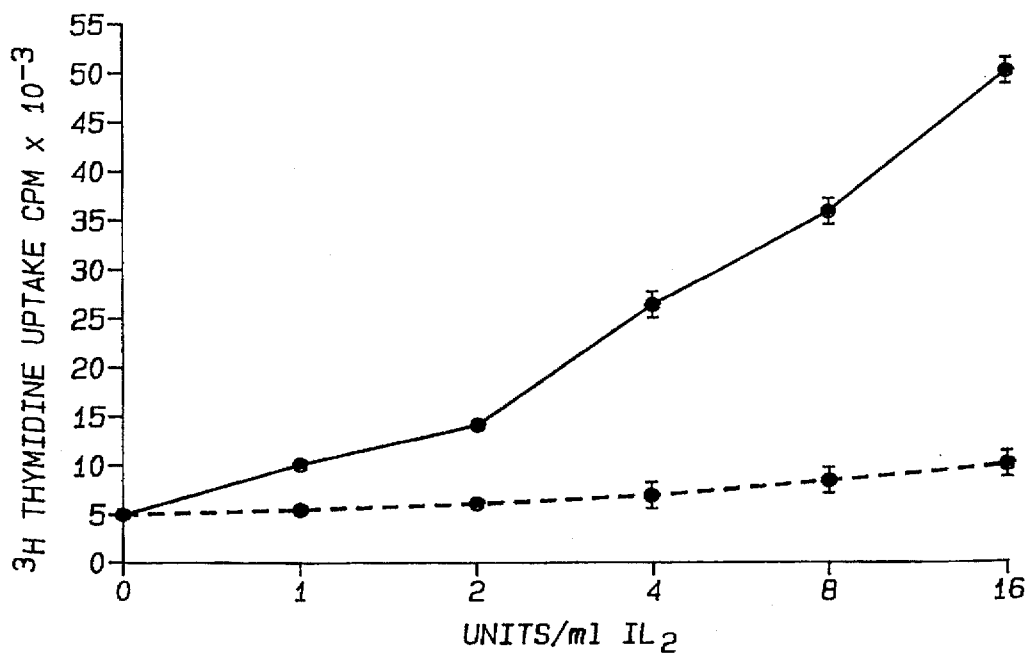
FIG. 4 is a dose response graph showing the effect on thymidine incorporation (ConA stimulation) of in vitro treatment of splenocytes from naive mice with NCM (solid line) compared to recombinant IL-2 (dashed line) at equivalent concentrations of IL-2.
Figure 5:
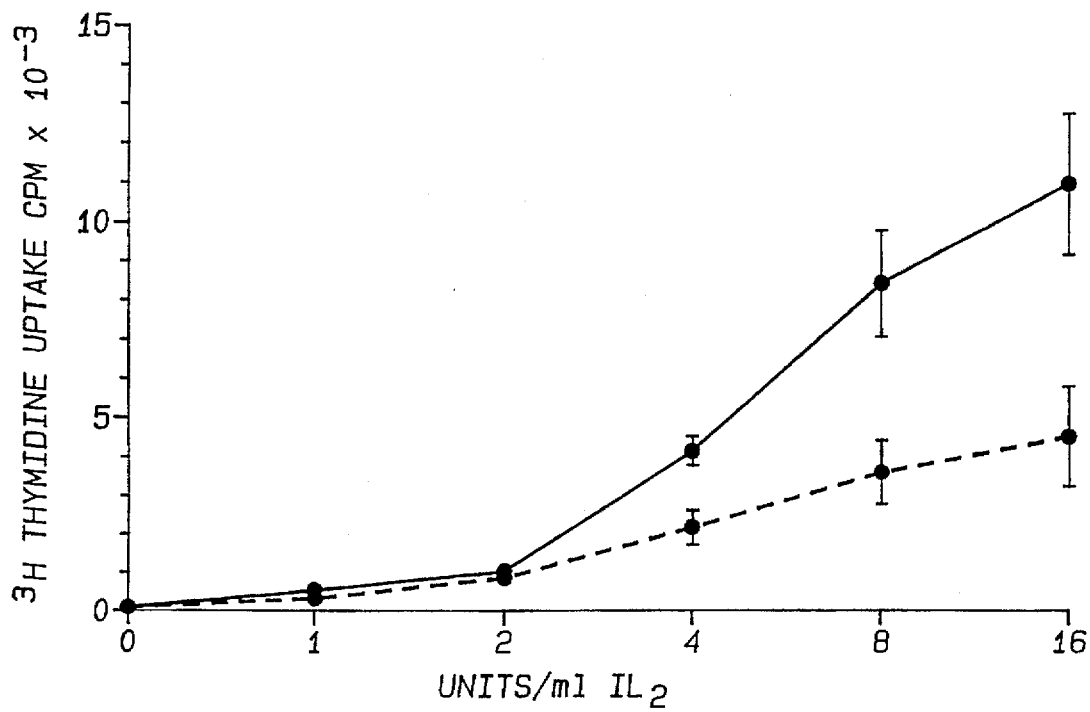
FIG. 5 is a dose-response graph showing the effect on thymidine incorporation of in vitro treatment of thymocytes from naive mice with NCM (solid line) compared to recombinant IL-2 (dashed line) at equivalent concentrations of IL-2.

In order to show the superiority of the NCM over rIL-1 in vitro, mouse splenocytes and thymocytes were cultured with MEM and rIL-2 at comparable levels of IL2 as determined by bioassay and DNA synthesis measured by tritiated thymidine incorporation. NCM induces greater proliferation of splenocytes (FIG. 4) and thymocytes (FIG. 5) then rIL-2 based on IL2 content.

Example 6

Figure 6:
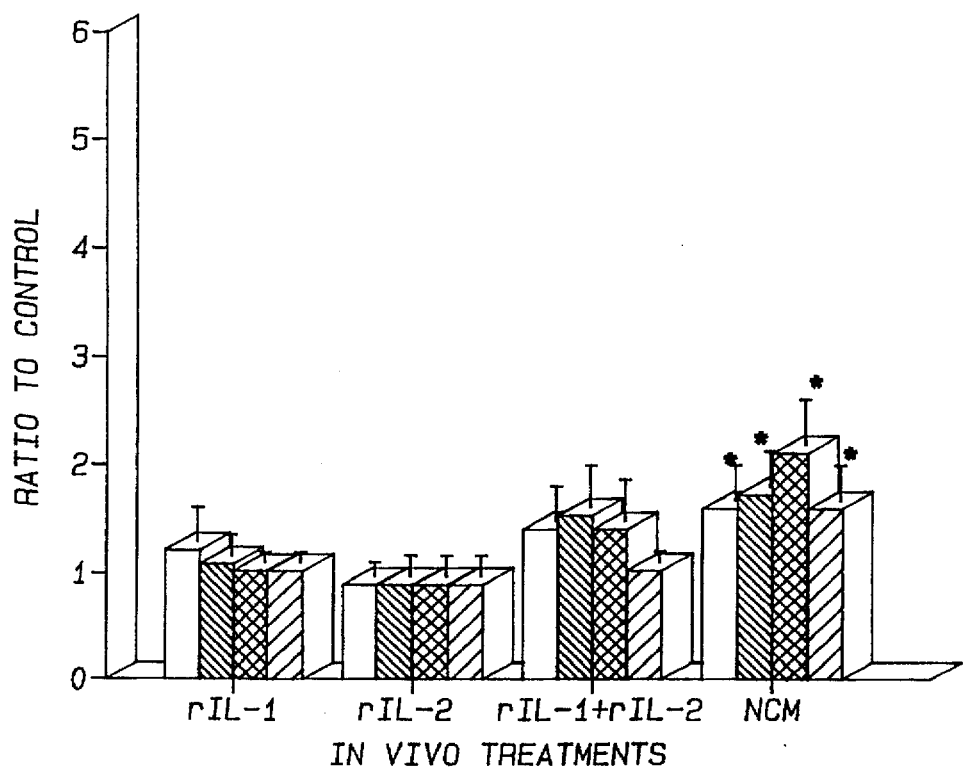
FIG. 6 is a bar graph of splenocyte responses in vitro to rIL-1 (open bar), rIL-2 (solid bar), NCM (cross-hatched) and concanavalin A (diagonal lines) after treatment in vivo with rIL-1, rIL-2, rIL-1+ rIL-2 or NCM.
Figure 7:
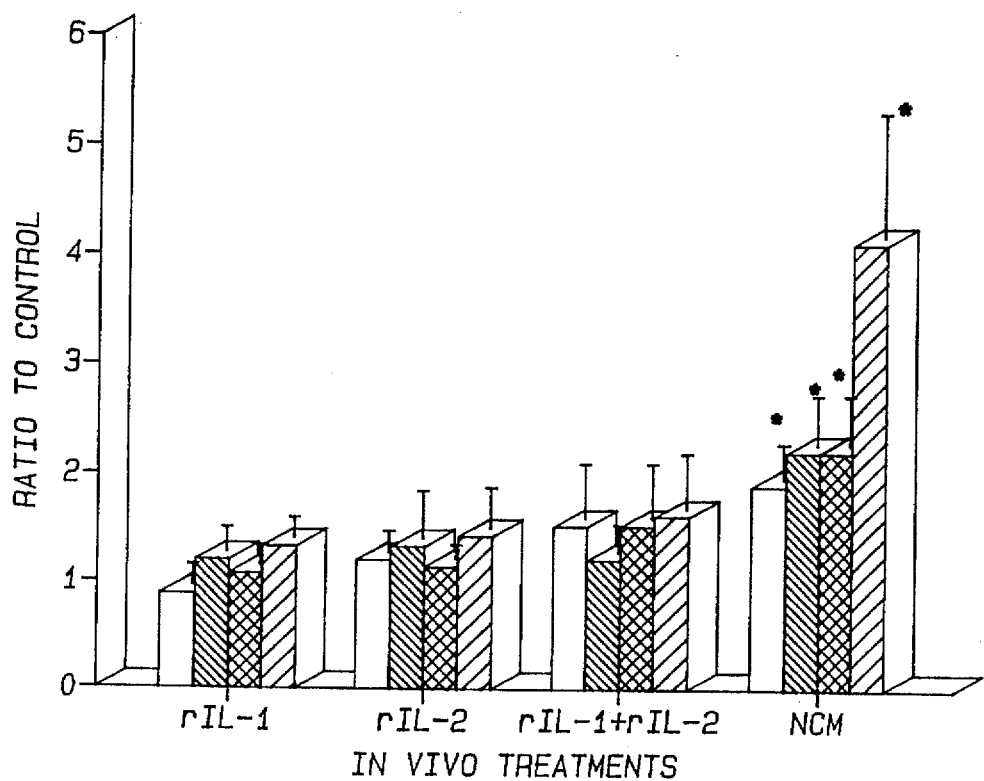
FIG. 7 is a bar graph of thymocyte responses in vitro to rIL-1, rIL-2, NCM and ConA after treatment in vivo as in FIG. 6.

In a series of experiments as set forth in FIGS. 6 and 7, mice with involuted thymuses were treated in vivo with rIL-1, rIL-2, combinations of these factors, NCM or saline (controls). The spleens and thymuses were removed, the cells tested for cell proliferation responses against the interleukins (IL-1, IL-2 ), NCM and the mitogen ConA. The results are expressed as ratio to the saline treated control. In vivo treatment with rIL-1, rIL-2, and their combination (rIL-1 and rIL-2 ) had no significant effect to increase proliferative responses of splenocytes (FIG. 6) or of thymocytes (FIG. 7) to in vitro stimulation with IL-1, IL-2, NCM or ConA. NCM treatment in vivo augmented significantly both splenocytes and thymocytes to all four stimuli. These results are consistent with an enhanced sensitivity of these cells to stimulation and/or an increase in the number of responsive cells.

Example 7

Figure 8:
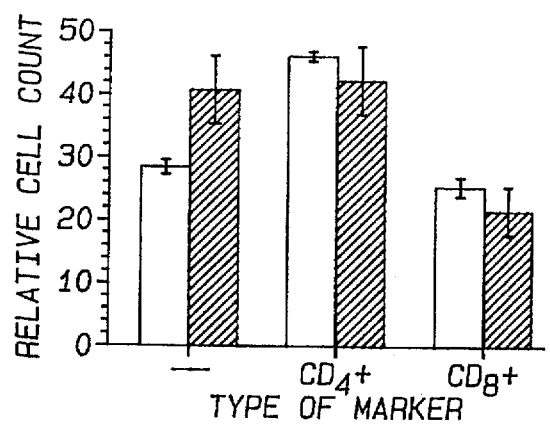
FIG. 8 is a bar graph showing the effect of in vivo treatment of mice with control (open bar) or NCM (solid bar) on splenocyte markers for $CD4^+$, $CD8^+$, and $CD4^-/CD8^-$ (—) cells.
Figure 9:
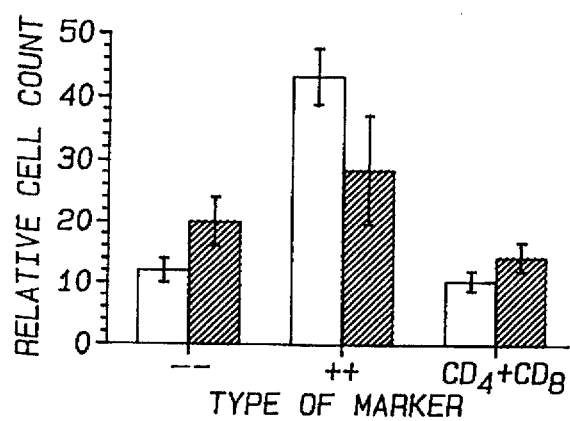
FIG. 9 is a bar graph showing the effect of in vivo treatment of mice with control (open bar) or NCM (solid bar) on thymocyte markers for $CD4^-/CD8^-$cells (—), $CD4^+/CD8^+$ (++) and $CD8^+$ and $CD4^+$ cells (CD4+CD8)

FIGS. 8 and 9 demonstrate the effect of NCM treatment in vivo on splenocyte and thymocyte markers. Non mature T-cells are indicated by — and may represent T lymphocyte precursors particularly in the thymus. NCM increased proportionately this population in spleen and thymus. Immature T-cells are indicated by ++ and this population is proportionately decreased in thymus by NCM treatment. Mature T-cells are indicated by CD4+ and CD8+. NCM increased the proportions of mature T-cells in thymus but not spleen. These results are consistent with an effect of NCM to increase T cell precursors and to promote their development to mature T cells in thymus.

Example 8

Figure 10:
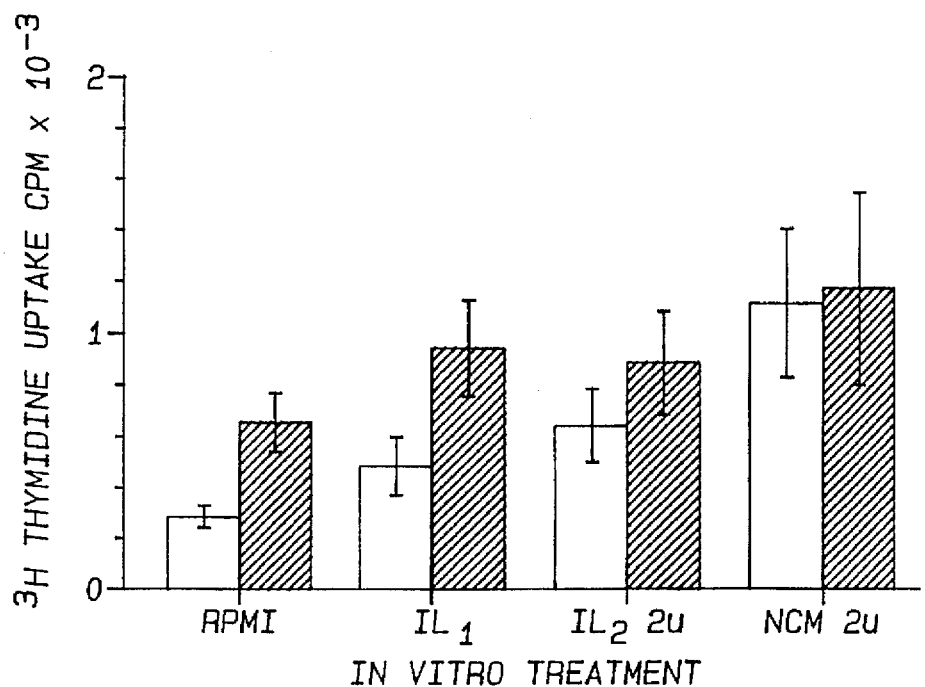
FIG. 10 is a bar graph of thymocyte responses in vitro to IL-1, IL-2 and NCM after treatment in vivo with control media (open bar) and NCM (closed bar)
Figure 11:
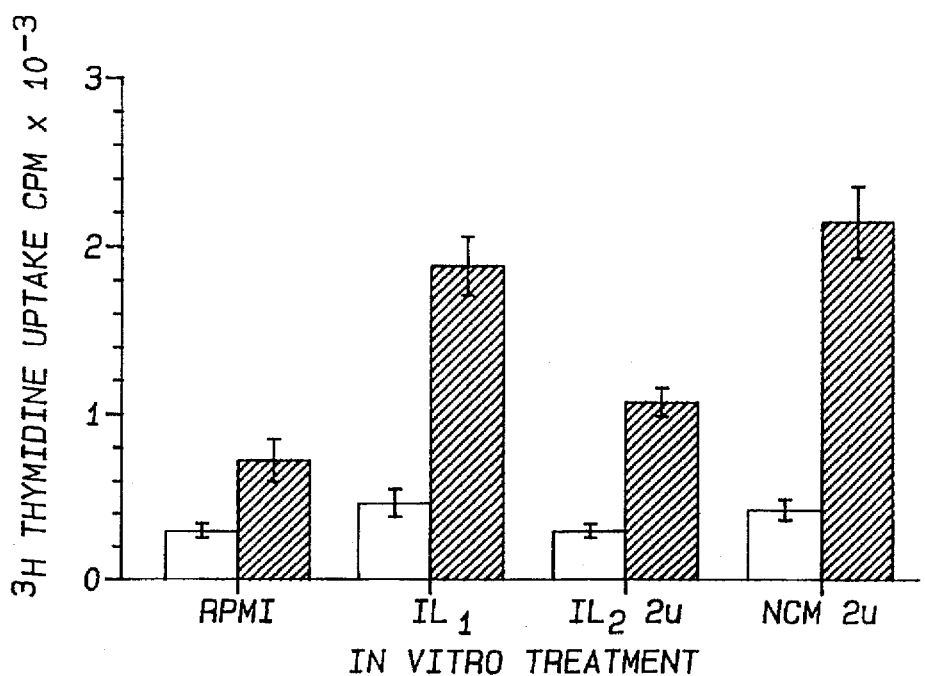
FIG. 11 is a bar graph of splenocyte responses as in FIG. 10.

FIGS. 10 and 11 demonstrate the splenocyte and thymocyte responses in vitro to media (RPMI), rIL-1 (IL1), rIL-2 ($IL_2$), or NCM after treatment in vivo with control media or NCM in the hydrocortisone model. The mice were treated as described hereinabove. These data demonstrate that NCM augments background splenocyte responses, splenocyte responses to IL-1 and IL-2, but not NCM and background thymocyte responses and thymocyte responses to IL-1, IL-2, and NCM.

Figure 12:
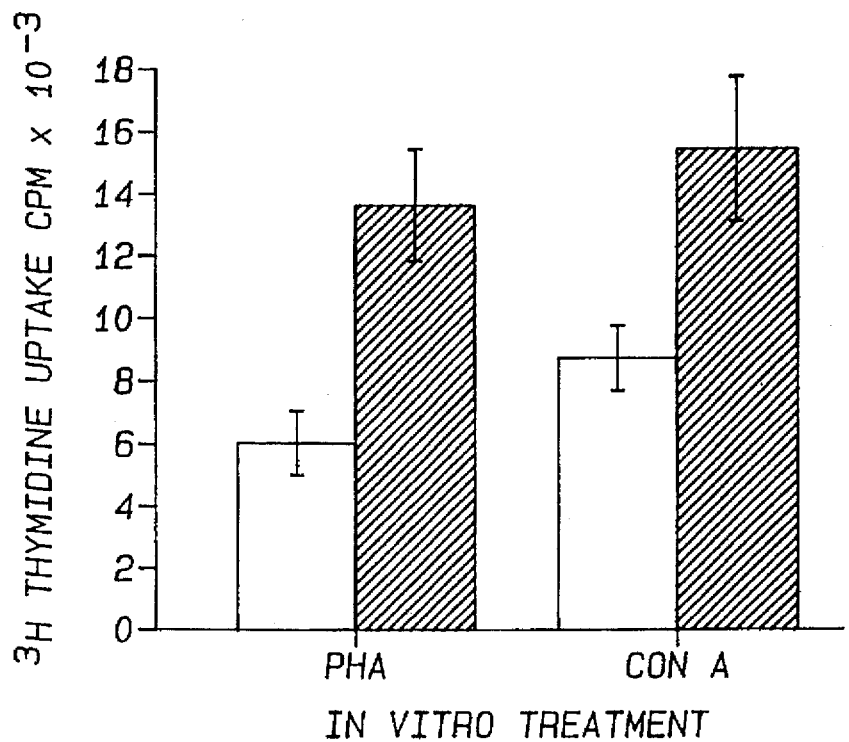
FIG. 12 is a bar graph of thymocyte responses in vitro to ConA and PHA after treatment in vivo with control media (open bar) and NCM (closed bar)
Figure 13:
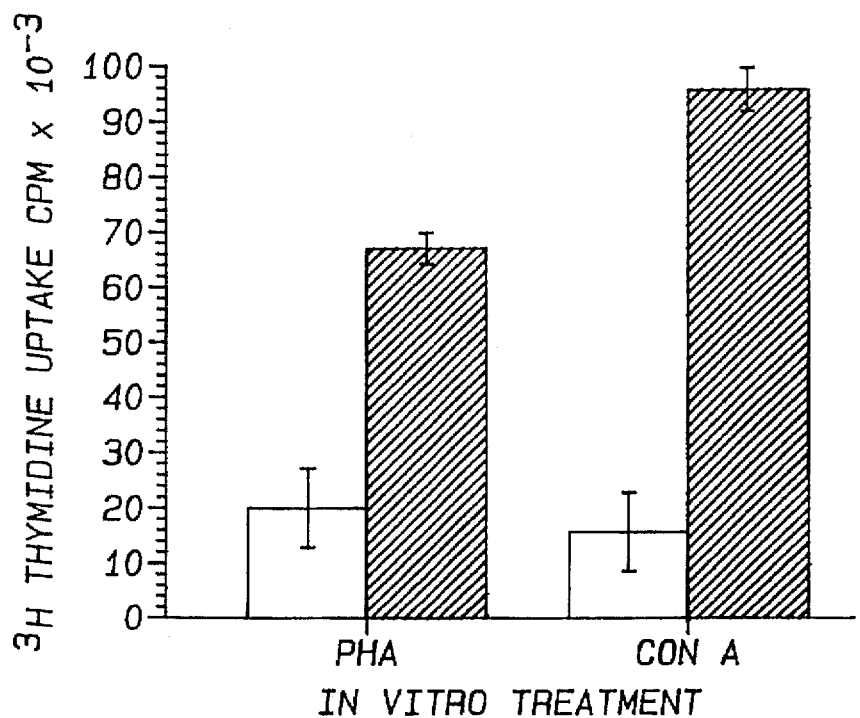
FIG. 13 is a bar graph of splenocyte responses as in FIG. 12.

FIGS. 12 and 13 demonstrate the splenocyte and thymocyte responses in vitro to ConA and PHA after treatment in vivo with control media or NCM. The mice were treated as described hereinabove.

The in vitro studies demonstrate the superiority of NCM over rIL-2 at equivalent doses in sensitizing splenocytes and thymocytes to proliferation signals. The effects on thymocytes reflect promotion of differentiation as well. The NCM composition, but not rIL-1, rIL-2, nor their combination, potently promotes in vivo T lymphocyte function (IL responses) and development (mitogen responses and cell markers) which is therapeutically relevant in any therapeutic measures requiring stimulation of the immune system or restoring even partial functioning of a damaged or defective immune system. For example chemotherapeutic agents can damage cells, including T lymphocytes, involved in the immune response. The present invention by stimulating the T lymphocyte functioning and development can restore, either partially or entirely, this feature of the immune system if damaged.

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

AIS Technical Bulletin No. 9003, "Covalent Immobilization of Antibodies to Protein-Reactive Polystyrene".

Belldegrun and Rosenberg, "Adoptive Immunotherapy of Urologic Tumors" Cancer Treat. Res 46:213–233, 1989.

Bender et al., "Absolute Peripheral Blood Lymphocyte Count and Subsequent Mortality of Elderly Men" JAGS 34:649–654, 1986

BioWhittaker Brochure, "Adoptive Immunotherapy and Genetic Therapy"

Borden, "Interferons: Rationale for Clinical Trials in Neoplastic Disease", Ann, Int. Med 91:492–479, 1979

Chang and Rosenberg, "Overview of Interleukin-2 as Immunotherapeutic Agent", Semin. Surg. Oncol. 5(6):385–90, 1989

Chilson and Kelly-Chilson, "Mitogenic Lectins Binds to the Antigen Receptor on Human Lymphocytes", Eur. J. Immunol., 19:389–396, 1989

Chirigos and Talmadge. Immunotherapeutic Agents: Their Role in Cellular Immunity and Their Therapeutic Potential. Springer Seminars in Immunopathol., 8:327–336, 1985

Cortesina et al., "Monoclonal Antibodies Against Epithelial Antigens . . . ", J. Laryngol Otol, 102(8):709–12, 1988

Cortesina et al., "Temporary Regression Of Recurrent Squamous Cell Carcinoma Of The Head And Neck Is Achieved With A Low But Not With A High Dose Of Recombinant Interleukin 2 Injected Perilymphatically", Br. J. Cancer, 69:572–576, 1994

Deans et al., "CD45R as a Primary Signal Transducer Stimulating IL-2 and IL-2R mRNA Synthesis by CD3⁻4⁻8⁻Thymocytes" J. Immunol., 143:242512430, 1989

DeSimone et al, "Report of the Symposium on the Use of Intravenous Gammaglobulin (IVIG) in Adults Infected with HIV", J. Clin. Lab. Anal. 4:313–317, 1990

Devos, "Molecular Cloning of Human Interleukin 2 cDNA and Its Expression in E.coli" Nucleic Acids Res., 11:4307–4323, 1983

Gillis et al. "T Cell Growth Factor: Parameters of Production and a Quantitive Microassay for Activity" J. Immunol., 120:2027–2032, 1978

Goldstein and Laslo, "The Role of Interferon in Cancer Therapy: A Current Perspective", Ca-A Cancer Journal For Clinicians 38:258–290, 1988

Hadden, "Immunotherapy of Human Immunodeficiency Virus (HIV)", TIPS, 12:107–111, 1991

Hadden, "Thymic Endocrinology" Int. J. Immunopharmacol., 14:345–352, 1992

Hadden, "Immunostimulants" Immunology Today 276, Vol 14, No. 6, 1993

Hadden, "T-Cell Adjuvancy", Int. J. Immunopharmacol., 1994

Hadden and Smith, "Immunopharmacology" JAMA, 268:2964–2969, 1992

Hadden et al. "Lymphocyte Blast Transformation. I. Demonstration of Adrenergic Receptors in Human Peripheral Lymphocytes", J. Cell. Immunol. 1:583–595, Hadden et al.,"Strategies of Immune reconstitution: Effects of Lymphokines on Murin T Cell Development in vitro and in vivo", Life Sci. 44:5–12, 1989

Hadden et al., "Characterization of Immunotherapeutic Agents" In Immunopharmology Reviews, Plenum Press, NY, p.1–64, 1990

Hadden et al., "Mixed Interleukins and Thymosin Fraction V Synergistically Induce T Lymphocyte Development in Hydrocortisone-Treated Aged Mice", Cell. Immunol. 144:228–236, 1992

Hadden et al. "Interleukins and Contrasuppression Induce Immune Regression of Head and Neck Cancer", Int. Arch. Otolaryngol., 120:395–403, 1994

Hall, "Immunomodulation with Intravenous Immunoglobulin", Pharmacotherapy, 13(6): 564–73, Nov-Dec 1993

Hwu and Rosenberg, "The Use of Gene-Modified Tumor-Infiltrating Lymphocytes for Cancer Therapy", Ann. N.Y. Acad. Sci. 716:188–203 1994a Hwu and Rosenberg, "The Genetic Modification of T Cells for Cancer Therapy: An Overview of Laboratory and Clinical Trials", Cancer Detect Prev. 18(1):43–50 1994b IGIV News Update, "An Extra Measure of Viral Safety" Vol. 1, No. 2 December 1993

June et al., "Evidence for the Involvement of Three Distinct Signals in the Induction of IL-2 Gene Expression in Human T Lymphocytes" J. Immunol., 143:153–161, 1989

Kameda et al., "Mixed Lymphokines in Low Dose Prolong Life in Cyclophosphamide-Treated Melanoma-Bearing Mice", Int. J. Immunother. 8:1–5, 1992

Lane and Fauci, "TherapeuticApproaches to the Undulying Immune Deficit in AIDS" Abstracts Int. Conf. on AIDS, Paris, 1986

Martorell, et al, "A Second Signal for T cell Mitogenesis Provided by Monoclonal Antibodies CD45 (T200)" Eur. J. Immunol. 17:1447–1451 (1987)

Mattijissen, "Clinical and Immunopathological Results of a Phase II Study of Perilymphaatically Injected Recombinant Interleukin-2 in Locally Far Advanced, Nonpretreated Head and Neck Squamous Cell Carcinoma". J. Immunother. 10:63–68, 1991

Merigan T.C., "Combination Anti HIV Therapy: Questions and Answers" in Combination Therapies 2 eds. Goldstein and Garaci, Plenum Press, pp.226–229, 1993

Mishell and Shiigi, Selected Methods Cellular Immunology, Freeman, pp. 23–24, 1981

Morgan et al. "Selective in vitro Growth of T Lymphocytes from Normal Human Boen Marrows" Science, 193:1007–8, 1976

Mule and Rosenberg, "Mechanistic Aspects of Successful Immunotherapy . . . " Prog. Clin. Biol., 244:79–91, 1987

Mutch and Hutson, "Levamisole in the Adjuvant Treatment of Colon Cancer", Clin. Pharmacol 10:95–109, 1991

Pulley et al., "Intravenous, Intralesional and Endolymphatic Administration of Lympokines in Human Cancer" Lymphokine Research, Vol. 5, Supplement 1, pp.S157–S163, 1986

Riesenbeck et al, "Superinduction of Cytokine Gene Transcription by Ciprofloxacin", J. Immunol. 153:343–352, 1994

Rosenberg et al., "Observatons on the Systemic Administration of Autologous Lymphokine-Activated Killer Cells and Recombinant Interleukin-2 to Patients with Metastatic Cancer", New Eng. J. Med. 313:1485–1492, 1985

Rosenberg, "The Development of New Immunotherapies for Treatment of Cancer using Interleukin-2", Ann Surg., 208 (2):121–135, August 1988

Rosenberg, "Immunotherapy of Cancer by Systemic Administration of Lymphoid Cells Plus Interleukin-2." J. Biol. Resp. Mod. 3:501–511, 1994

Spreafico, "Use of Levamisole in Cancer Patients", Drugs 19:105–116, 1980

Symoens and Rosenthal, "Levamisole in the Modulation of Immune Response: The Current Experimental and Clinical State", J. Reticuloendothel. Soc. 21:175–219, 1977

Talmadge et al., Screening for Biological Response Modifiers: Methods and Rationale, Martinus Nijhoff, Boston, p. 121–129 & 181–182, 1985

Talmadge and Hadden, "An Update on Immunopharmacology of Recombinant and Synthetic Bilogical Response Modifiers" in: Immunoregulators in therapy of disease (Marcel Dekker, NY) 1993, in press Taniguchi et al. "Structure and Expression of a Cloned cDNA for Human Interleukin-2" *Nature*, 302:305–310, 1983

Thurman et al., *J. Biol. Response Modif.*, 5:85–107, 1986

Webb et al., "Mitogen-Induced Human Lymphocyte Activation in Serum-Free Medium" *Clinical Immunology and Immunopathology*, 1:304–310, 1973

What is claimed is:

1. A method of producing a nonrecombinant cytokine mixture with interleukin IL-2 present at 100–500 units/ml and interleukin IL-3 and interleukin IL-4 present in trace amounts including the steps of immobilizing phytohemaglutinin in a tissue culture vessel, suspending an isolated population of lymphocytes free of neutrophils and erythrocytes, in a serum-free media certified for human use, placing the suspended lymphocytes in the vessel, culturing the lymphocytes, removing the media, and characterizing the removed media for yield of cytokines wherein interleukin IL-2 is present at 100–500 units/ml and interleukin IL-3, interleukin IL-4, interleukin IL-7 are present in trace amounts.

2. A method according to claim 1 wherein the serum free media is selected from serum free media X vivo-10 and serum free media X vivo-15, each of which media is certified for human use.

3. A method according to claim 1 wherein the serum free media contains a 4-aminoquinolone antibiotic.

4. A method according to claim 3 wherein the 4-aminoquinolone antibiotic is selected from the group consisting of Ciprofloxacin, Norfloxacin and Ofloxacin.

5. A method according to claim 1 wherein the tissue culture vessel is a surface activated cell culture AIS MICROCELLECTOR™ T-25 flasks.

6. A method according to claim 1 wherein the culturing is for twenty-four to forty-eight hours.

7. The method of claim 1 further characterized by the step of isolating the cytokines from the removed media containing the cytokines.

8. A method of producing an in vitro nonrecombinant cytokine mixture with interleukin IL-2 present at 100–500 units/ml and interleukin IL-3 and interleukin IL-4 present in trace amounts whereby the removed media containing the cytokines is mitogen-free and is used directly as a medicament without concentrating including the steps of immobilizing phytohemaglutinin in a tissue culture vessel;

suspending an isolated population of lymphocytes free of neutrophils and erythrocytes in a serum-free media certified for human use containing a 4-aminoquinolone antibiotic;

placing the suspended lymphocytes in the media in the vessel;

culturing the lymphocytes;

removing the media; and characterizing the removed media for yield of cytokines wherein interleukin IL-2 is present at 100–500 units/ml and interleukin IL-3, interleukin IL-4, interleukin IL-7 are present in trace amounts whereby the removed media containing the cytokines is mitogen-free and is used directly as a medicament without concentrating.

9. A nonrecombinant mixture of cytokines produced by culturing lymphocytes in a serum-free medium certified for human use in the presence of immobilized phytohemagglutinin and containing a cytokine profile of interleukin IL-1 at 10–2000 pg/ml, interleukin IL-2 at 100–500 units/ml, interleukin IL-6 at 250–10,000 pg/ml, interleukin IL-8 at 12,000–100,000 pg/ml, interleukin IL-12 at 100–10,000 pg/ml, interferon IFN-γ at 50–15,000 pg/ml, tumor necrosis factor TNF-α at 50–15,000 pg/ml, colony stimulating factor CSF-G at 50–1500 pg/ml, colony stimulating factor CSF-GM at 10–1500 pg/ml, and interleukin IL-3, interleukin IL-4, interleukin IL-7 present in trace amounts whereby the cytokine profile stimulates T-helper cells Type I.

* * * * *